United States Patent
Kim et al.

(10) Patent No.: US 10,991,094 B2
(45) Date of Patent: Apr. 27, 2021

(54) METHOD OF ANALYZING DENTAL IMAGE FOR CORRECTION DIAGNOSIS AND APPARATUS USING THE SAME

(71) Applicant: DDH INC., Seoul (KR)

(72) Inventors: Han Suk Kim, Suwon-si (KR); Yeong Sung Yu, Cheonan-si (KR); Shin Jae Lee, Goyang-si (KR)

(73) Assignee: DDH INC., Seoul (KR)

( * ) Notice: Subject to any disclaimer, the term of this patent is extended or adjusted under 35 U.S.C. 154(b) by 81 days.

(21) Appl. No.: 16/347,132

(22) PCT Filed: Oct. 11, 2018

(86) PCT No.: PCT/KR2018/011969
§ 371 (c)(1),
(2) Date: May 2, 2019

(87) PCT Pub. No.: WO2020/040349
PCT Pub. Date: Feb. 27, 2020

(65) Prior Publication Data
US 2020/0286223 A1    Sep. 10, 2020

(30) Foreign Application Priority Data

Aug. 21, 2018 (KR) ........................ 10-2018-0097713

(51) Int. Cl.
| | |
|---|---|
| *G06T 7/00* | (2017.01) |
| *G06T 7/143* | (2017.01) |
| *G06T 7/13* | (2017.01) |
| *G16H 30/20* | (2018.01) |
| *G16H 50/20* | (2018.01) |
| *A61B 6/14* | (2006.01) |
| *G06N 3/08* | (2006.01) |

(52) U.S. Cl.
CPC .............. *G06T 7/0012* (2013.01); *A61B 6/14* (2013.01); *G06N 3/08* (2013.01); *G06T 7/13* (2017.01);
(Continued)

(58) Field of Classification Search
CPC ......... G06T 7/0012; G06T 7/143; G06T 7/13; G06T 2207/20081; G06T 2207/20084;
(Continued)

(56) References Cited

U.S. PATENT DOCUMENTS

| | | | |
|---|---|---|---|
| 10,049,457 B2* | 8/2018 | Abraham | ................ A61B 6/14 |
| 2004/0184643 A1* | 9/2004 | Stantchev | ................ A61B 6/14 |
| | | | 382/128 |

(Continued)

FOREIGN PATENT DOCUMENTS

KR    20170142572 A    * 12/2017

OTHER PUBLICATIONS

Hansang Lee, Cephalometric landmark detection in dental x-ray images using convolutional neural networks, Mar. 3, 2017, Proc. SPIE 10134, Medical Imaging, p. 101341W-1-101341W-6. (Year: 2017).*

(Continued)

*Primary Examiner* — Brenda C Bernardi
(74) *Attorney, Agent, or Firm* — Novick, Kim & Lee, PLLC; Sang Ho Lee

(57) ABSTRACT

Provided is a method of analyzing a dental image for a correction diagnosis and an apparatus using the same. The method includes the steps of obtaining a dental image of an examinee and detecting at least some of a plurality of landmarks for a correction diagnosis in the dental image using a landmark detection module, wherein the landmark is an anatomical reference point indicative of a relative position of at least one of a facial skeleton, a tooth and a face contour necessary for t correction diagnosis, and the landmark detection module may include a machine learning module based on an artificial neural network.

12 Claims, 11 Drawing Sheets

(52) U.S. Cl.
CPC .............. *G06T 7/143* (2017.01); *G16H 30/20* (2018.01); *G16H 50/20* (2018.01); *G06T 2207/20081* (2013.01); *G06T 2207/20084* (2013.01); *G06T 2207/30036* (2013.01); *G06T 2207/30201* (2013.01)

(58) Field of Classification Search
CPC ........... G06T 2207/30036; G06T 2207/30201; G16H 30/20; G16H 50/20; A61B 6/14; G06N 3/08
See application file for complete search history.

(56) References Cited

U.S. PATENT DOCUMENTS

| | | | | |
|---|---|---|---|---|
| 2009/0003667 | A1* | 1/2009 | Cheng | G06T 7/60 382/128 |
| 2012/0172700 | A1* | 7/2012 | Krishnan | A61B 6/517 600/407 |
| 2016/0038092 | A1* | 2/2016 | Golay | A61C 8/00 433/24 |
| 2016/0203604 | A1* | 7/2016 | Gupta | A61C 7/002 382/128 |
| 2016/0284089 | A1* | 9/2016 | Gulaka | G06T 7/33 |
| 2019/0025858 | A1* | 1/2019 | Bar-Nahum | B64D 47/08 |
| 2019/0125295 | A1* | 5/2019 | Tek | A61B 8/483 |
| 2019/0333627 | A1* | 10/2019 | Johnson | G16H 50/20 |
| 2020/0013162 | A1* | 1/2020 | Yum | G06K 9/52 |

OTHER PUBLICATIONS

Sercan Arik, Fully automated quantitative cephalometry using convolutional neural networks, Jan. 2017, Journal of Medical Imaging, vol. 4(1), p. 014501-1-014501-11. (Year: 2017).*

Rosalia Leonardi, An Evaluation of Cellular Neural Networks for the Automatic Identification of Cephalometric Landmarks on Digital Images, Sep. 10, 2009, vol. 2009, p. 1-12. (Year: 2009).*

* cited by examiner

METHOD OF ANALYZING DENTAL IMAGE FOR CORRECTION DIAGNOSIS AND APPARATUS USING THE SAME

TECHNICAL FIELD

The present invention relates to a method of analyzing a dental image for correction diagnosis and an apparatus using the same and, more particularly, to a method for analyzing a dental image, which can detect a plurality of landmarks for correction diagnosis precisely and rapidly in a dental image through a machine learning module, and an apparatus using the same.

BACKGROUND ART

Generally, occlusion means the state in which the teeth of the upper and lower jaws are engaged when a mouth is shut. Furthermore, malocclusion means an inaccurate occlusal relation in which the array of teeth is not uniform due to some reason or means a functional and esthetic problem caused by an engagement state of the upper and lower jaws which deviates from a normal position.

In this case, it has been known that malocclusion is greatly caused by a genetic influence, but may also occur due to various causes, such as a problem in the shape or size of teeth, environmental influence, poor habits, erroneous posture, and a congenital disorder such as dental caries.

When malocclusion occurs, food residues often remain between teeth because the set of the teeth is not uniform. Furthermore, since hygiene management using accurate toothbrushing is not easy, dental plaque within an oral cavity increases and may proceed to cause dental caries or a gum disease such as gum infection. Moreover, if there is a tooth which greatly deviates from a normal set of teeth or if the position of a jaw is abnormal, there is a good possibility that the tooth may be damaged, such as odontoclasis, when an external shock is applied.

Accordingly, correction treatment is performed to treat malocclusion. In this case, orthodontic treatment uses a property of a tooth which moves when an external force is applied to the tooth. Correction treatment may be performed using various devices and methods depending on a cause or treatment time. For example, the devices may be classified into devices for suppressing or enhancing the development of upper and lower jawbones or devices for slowly moving a tooth to a desired position.

In order to properly perform such correction treatment on a patient, a determination of the patient's face shape must be first made. For such a face shape determination (i.e., correction diagnosis), a cephalometric analysis method shown in FIG. 1 is chiefly used.

Cephalometric analysis is a method for determining a face shape for correction treatment using anatomical reference points indicative of relative positions, such as a facial skeleton, tooth or face contour. In a conventional technology, an orthotic doctor directly marks necessary reference points manually while viewing the cephalogram of a patient that requires correction treatment and determines a face shape of the patient based on relative angles of straight lines to connect the reference points.

However, such a conventional method is a method of an orthotic doctor to subjectively mark the necessary reference points based on his or her own academic experience. Consequently, the method has problems in that the standardization and sharing of reference points are difficult because reference points used for a face shape determination are different for each orthotic doctor, a lot of time is consumed because an orthotic doctor must manually mark multiple reference points one by one, and there is a deviation in accuracy depending on a skill level of the orthotic doctor.

Therefore, there is a need for a method of analyzing a dental image for correction diagnosis, which can solve the conventional problems.

DISCLOSURE

Technical Problem

The present invention has been made to solve the above problems and an object of the present invention is to provide a method for analyzing a dental image, which can detect a plurality of landmarks for correction diagnosis precisely and rapidly in a dental image through a machine learning module, and an apparatus using the same.

Technical objects to be achieved in the present invention are not limited to the aforementioned technical object, and other technical objects not described above may be evidently understood by a person having ordinary skill in the art to which the present invention pertains from the following description.

Technical Solution

According to an embodiment of the present invention, there is provided a method of analyzing a dental image for correction diagnosis. The method the steps of obtaining a dental image of an examinee and detecting at least some of a plurality of landmarks for correction diagnosis in the dental image using a landmark detection module, wherein the landmark is an anatomical reference point indicative of a relative position of at least one of a facial skeleton, a tooth and a face contour necessary for correction diagnosis, and the landmark detection module may include a machine learning module based on an artificial neural network.

Preferably, the method further includes the step of training the machine learning module using training data comprising a plurality of accumulated comparison dental images. The comparison dental image may be a dental image of a different examinee whose landmark has been read by a medical specialist.

Furthermore, preferably, the dental image may be cephalogram.

Furthermore, preferably, in the step of detecting at least some of the landmarks, the landmark detection module may detect the plurality of landmarks based on a single convolution network.

Furthermore, preferably, the step of detecting at least some of the landmarks may include the steps of detecting a plurality of boundary boxes predicted to include at least some of anatomical features corresponding to the plurality of landmarks, respectively, and determining a specific point included in a boundary box to be a landmark with respect to each of at least some of the detected boundary boxes.

Furthermore, preferably, the step of detecting at least some of the landmarks may further include the step of resizing the received dental image, and the detecting step may be performed based on the resized dental image.

Furthermore, preferably, the step of detecting at least some of the landmarks may further include the step of calculating a presence probability of an individual anatomical feature with respect to each of the boundary boxes. The step of determining the specific point may include the steps of filtering one of a plurality of boundary boxes corresponding to one individual anatomical feature based on the presence probability when the plurality of boundary boxes may be detected with respect to the one individual anatomical feature and determining a specific point included in the filtered boundary box to be the landmark.

Furthermore, preferably, in the determining step, center coordinates may be determined to be the landmark with respect to at least some of the detected boundary boxes.

Furthermore, preferably, the method may further include the steps of identifying a landmark whose detection has been omitted by comparing the detected landmark with a plurality of preset landmarks; searching for a standard dental image having a standard landmark corresponding to at least some of the detected landmarks based on standard landmark information, wherein the standard landmark information comprises information about a plurality of the standard dental images and a plurality of the standard landmarks read with respect to each of the plurality of standard dental images; and determining the position of the omitted landmark using the retrieved standard dental image and the standard landmark of the retrieved standard dental image.

Furthermore, preferably, the standard landmark information may further include information about a plurality of adjacent landmarks disposed close to the respective standard landmark. In the step of searching for the standard dental image, the standard dental image having a set of standard landmarks corresponding to a set of adjacent landmarks adjacent to the omitted landmark among the detected plurality of landmarks may be searched for based on information about the adjacent landmarks.

Furthermore, preferably, the standard dental image may be generated by extracting a presence area of the standard landmark from an original dental image. The information about the standard landmark may include information about the relative coordinates of the standard landmark in the standard dental image. The method may further include the step of calculating the relative coordinates of the detected landmark by extracting the presence area of the detected landmark from the dental image and normalizing the extracted area at the same scale as the standard dental image. The step of searching for the standard dental image and the step of determining the position of the omitted landmark may be performed based on the relative coordinates of the detected landmark and the relative coordinates of the standard landmark.

Furthermore, preferably, the method may further include the steps of receiving preference landmark information of a diagnostician and emphasizing and displaying some of the detected landmarks corresponding to the preference landmark information.

Furthermore, preferably, the method may further include the step of determining a face shape of the examinee for correction treatment by performing cephalometric analysis based on the detected landmark.

According to an embodiment of the present invention, there is provided a computer-readable recording medium in which a program for performing the method is written.

According to an embodiment of the present invention, there is provided a computing device supporting the analysis of a dental image for correction diagnosis. The device includes a communication unit obtaining a dental image of an examinee and a processor comprising a landmark detection module for detecting at least some of a plurality of landmarks for correction diagnosis from the dental image. The landmark is an anatomical reference point indicative of a relative position of at least one of a facial skeleton, a tooth and a face contour necessary for correction diagnosis, and the landmark detection module may include a machine learning module based on an artificial neural network.

Advantageous Effects

In accordance with an embodiment of the present invention, the accuracy of correction diagnosis, convenience and rapidness can be enhanced because 80 landmarks or more from a dental image of an examinee are automatically provided as a work level of an experienced medical resident using the machine learning module based on an artificial neural network.

DESCRIPTION OF DRAWINGS

A brief description of each drawing is provided so that the drawings quoted in the detailed description of the present invention are understood more fully.

MODE FOR INVENTION

Figure 1:
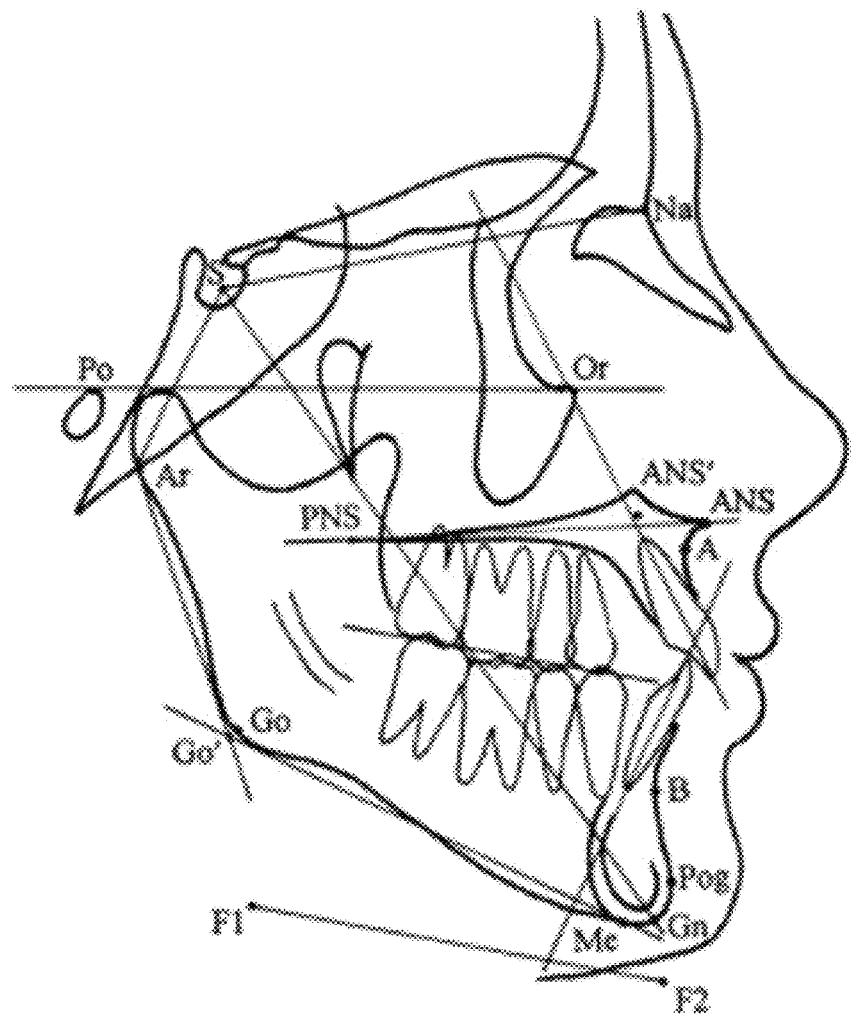
FIG. 1 schematically shows a conventional cephalometric analysis method.

Hereinafter, embodiments according to the present invention are described with reference to the accompanying drawings. It is to be noted that in assigning reference numerals to elements in the drawings, the same elements have the same reference numerals even in cases where the elements are shown in different drawings. Furthermore, in describing the embodiments of the present invention, a detailed description of the known elements or functions will be omitted if it is determined that the detailed description hinders understanding of the embodiments of the present invention. Furthermore, hereinafter, embodiments of the present invention will be described, but the technical spirit of the present invention is not limited or restricted thereto and may be modified and practiced in various ways by those skilled in the art.

Throughout this specification, when it is described that one part is "connected" to the other part, the one part may be "directly connected" to the other part or "indirectly connected" to the other part through another element. Furthermore, when it is described that any part "includes" any element, it means that the part does not exclude other elements unless specially defined otherwise, but may further include other elements. Furthermore, in describing the elements of the embodiments of the present invention, terms, such as the first, the second, A, B, (a), and (b), may be used. However, although the terms are used only to distinguish one element from the other element, the essence, order, or sequence of the elements is not limited by the terms.

Figure 2:
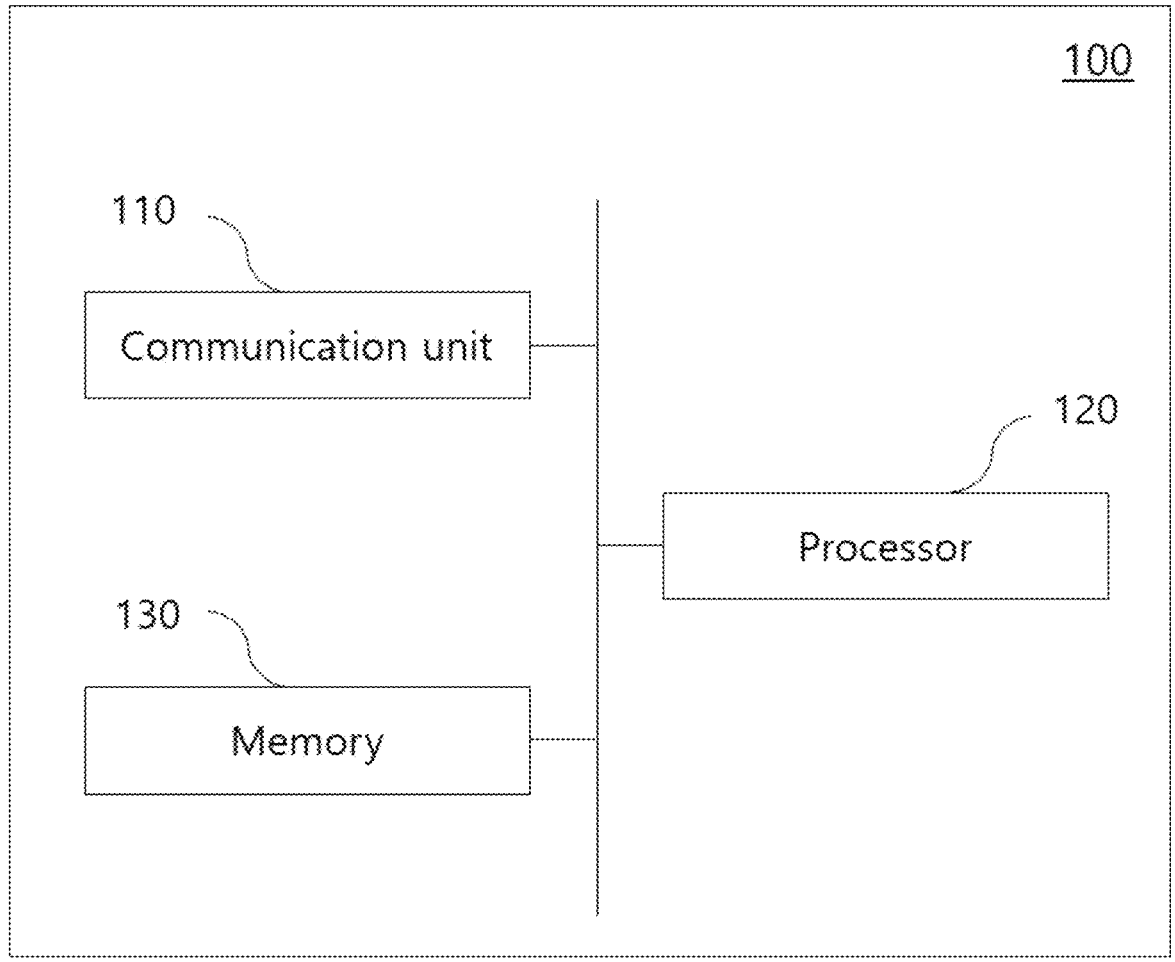
FIG. 2 shows an exemplary configuration of a computing device which performs a method of analyzing a dental image for correction diagnosis according to an embodiment of the present invention.

FIG. 2 shows an exemplary configuration of a computing device which performs a method of analyzing a dental image for correction diagnosis according to an embodiment of the present invention.

The computing device 100 according to an embodiment of the present invention includes a communication unit 110, a processor 120 and a storage unit 130, and may communicate with an external computing device (not shown) through the communication unit 110 directly or indirectly.

Specifically, the computing device 100 may achieve required system performance using a combination of a typical computer hardware (e.g., a computer processor, memory, storage, an input device and output device, and a device that may include elements of the existing computing device; electronic communication devices such as a router and a switch; electronic information storage systems such as network attached storage (NAS) and storage area network (SAN)) and computer software (i.e., instructions that enable the computing device to function as a specific method).

The communication unit 110 of the computing device 100 may transmit and receive requests and responses to and from other computing devices operating in conjunction thereto. For example, such a request and response may be performed by the same TCP session, but are not limited thereto. For example, such a request and response may be transmitted and received as an UDP datagram. In addition, in a broad sense, the communication unit 110 may include a keyboard, a mouse and other external input devices for receiving a command or instruction.

Furthermore, the processor 120 of the computing device 100 may include hardware elements, such as a micro processing unit (MCU) or a central processing unit (CPU), cache memory, and a data bus. Furthermore, the processor may further include an operating system and a software element of an application that performs a specific objective.

Furthermore, the storage unit 130 of the computing device 100 may store various data involved in an operation of the computing device 100. As known to those skilled in the art, the storage unit 130 may be implemented as storage devices of various forms capable of information input and output, such as a hard disk drive (HDD), read only memory (ROM), random access memory (RAM), electrically erasable and programmable read only memory (EEPROM), flash memory, a compact flash (CF) card, a secure digital (SD) card, a smart media card, a multimedia card (MMC) or a memory stick. The storage unit may be provided within the computing device 100 or may be provided in a separate device.

Figure 3:
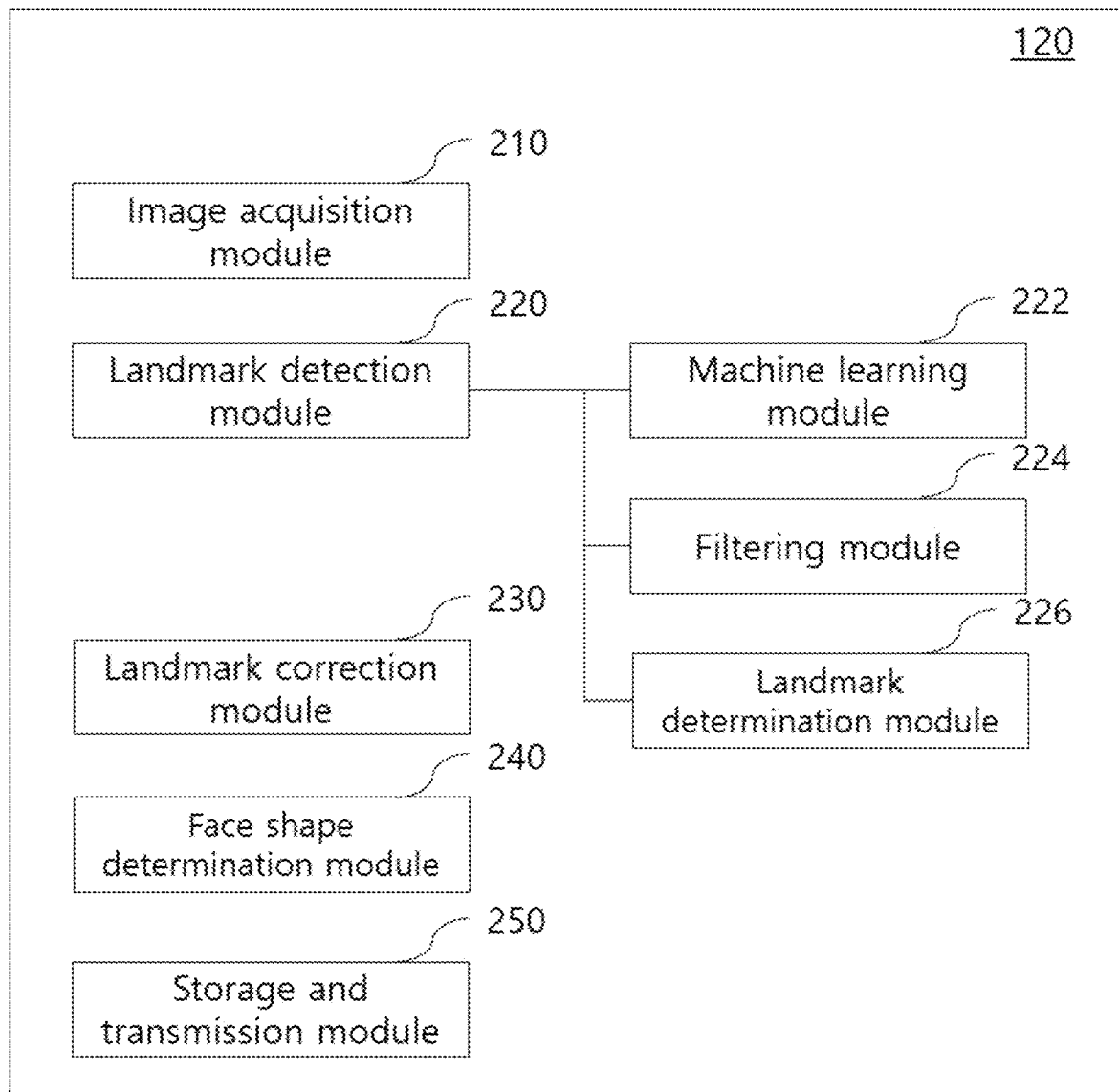
FIG. 3 illustrates hardware and software architecture of the computing device which performs a method of analyzing a dental image for correction diagnosis according to the present invention.

FIG. 3 illustrates hardware and software architecture of the computing device which performs a method of analyzing a dental image for correction diagnosis according to the present invention.

Referring to FIG. 3, the processor 120 of the computing device 100 according to an embodiment of the present invention may include an image acquisition module 210, a landmark detection module 220, a landmark correction module 230, a face shape determination module 240 and a storage and transmission module 250. For example, each of the modules may be implemented to operate by the interoperation of the processor 120 and the communication unit 110 and/or the storage unit 130.

The image acquisition module 210 may obtain a dental image of an examinee from a different external computing device or another device (a dental image photographing device, etc.) operating in conjunction with the computing device 100 through the communication unit 110. In this case, the dental image may be cephalogram obtained by photographing the side of the head of an examinee using X-rays.

The landmark detection module 220 may detect from a dental image a plurality of landmarks necessary for correction diagnosis. In this case, the plurality of landmarks denotes anatomical reference points indicative of a relative position of at least one of a facial skeleton, a tooth and a face contour necessary for the correction diagnosis. The plurality of landmarks may include N number of landmarks according to a user's setting or by default, and may preferably include 80 landmarks.

The landmark detection module 220 may include a machine learning module 222, a filtering module 224, and a landmark determination module 226.

The machine learning module 222 has been implemented to detect a plurality of objects at the same time from a video or an image, and may be implemented based on an artificial neural network, in particular, on a Convolution Neural Network (CNN) or an artificial neural network modified/improved from the CNN.

In one embodiment, the machine learning module 222 may be implemented as a single convolution network to enable rapid and simultaneous detection for a plurality of objects. For example, an artificial neural network implemented by the You Only Look Once (YOLO) algorithm may be applied, but the present invention is not limited thereto. In embodiments to which the present invention is applied, various algorithms or artificial neural networks suitable for detecting a plurality of objects, such as an SSD and an R-CNN, may be applied.

The machine learning module 222 may include a plurality of convolution layers and a fully connected layer. In this case, the plurality of convolution layers may be implemented to extract features by abstracting an image. The fully connected layer may be implemented to predict the probability that a detection object is output and to predict the coordinates of a boundary box in which the object is detected.

In the present invention, the machine learning module 222 may identify (or detect) anatomical features corresponding to a plurality of landmarks in a dental image through a boundary box. For example, the machine learning module 222 may split a dental image into a plurality of cells, and may assign a specific number of boundary boxes with respect to each cell. If an individual anatomical feature is present in a specific cell, a boundary box assigned to the corresponding cell may be implemented to identify the individual anatomical feature.

Accordingly, the machine learning module 222 may predict a boundary box in which an individual anatomical feature corresponding to a plurality of landmarks are present, the coordinates and size of a corresponding boundary box, the probability that each individual anatomical feature will be present within the boundary box, etc. from a dental image.

The filtering module 224 may filter a boundary box detected by the machine learning module 222 based on the presence probability of an individual anatomical feature. Specifically, when two or more boundary boxes are detected with respect to one individual anatomical feature, the filtering module 224 may select one of the two or more boundary boxes as the boundary box in which the corresponding individual anatomical feature is present based on a presence probability.

The landmark determination module 226 may determine a specific point included in each of the finally selected the boundary boxes to be a landmark by incorporating the results of filtering. For example, the landmark determination module 226 may be implemented to determine the center coordinates of each boundary box as a landmark.

The landmark correction module 230 may identify whether a landmark omitted by the landmark detection module 220 is present, and may predict the position (or coordinates) of the omitted landmark using standard landmark information. In this case, the standard landmark information may include information about a plurality of standard dental images, a plurality of standard landmarks read with respect to the plurality of standard dental images, respectively, and/or a plurality of adjacent landmarks disposed close to the respective standard landmarks.

The face shape determination module 240 may classify or determine a face shape of an examinee for correction treatment by performing cephalometric analysis based on at least some of the finally detected landmarks. A diagnostician can work out a future correction treatment plan for the examinee based on the determined face shape.

The storage and transmission module 250 may store training data (e.g., a comparison dental image) for the learning of the machine learning module 222, a dental image of an examinee and the results of detection of landmarks in the storage unit 130, and may transmit them to an external computing device, a display device, etc., through the communication unit 110.

Figure 4:
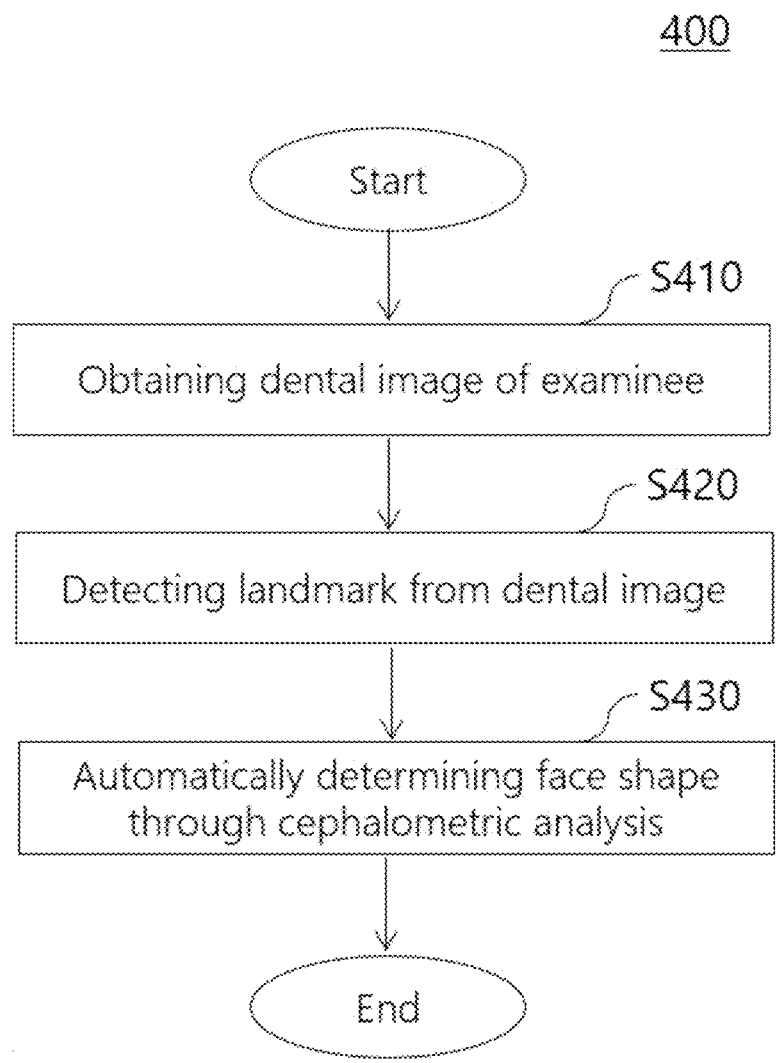
FIG. 4 shows a method of analyzing a dental image for correction diagnosis according to an embodiment of the present invention.
Figure 5:
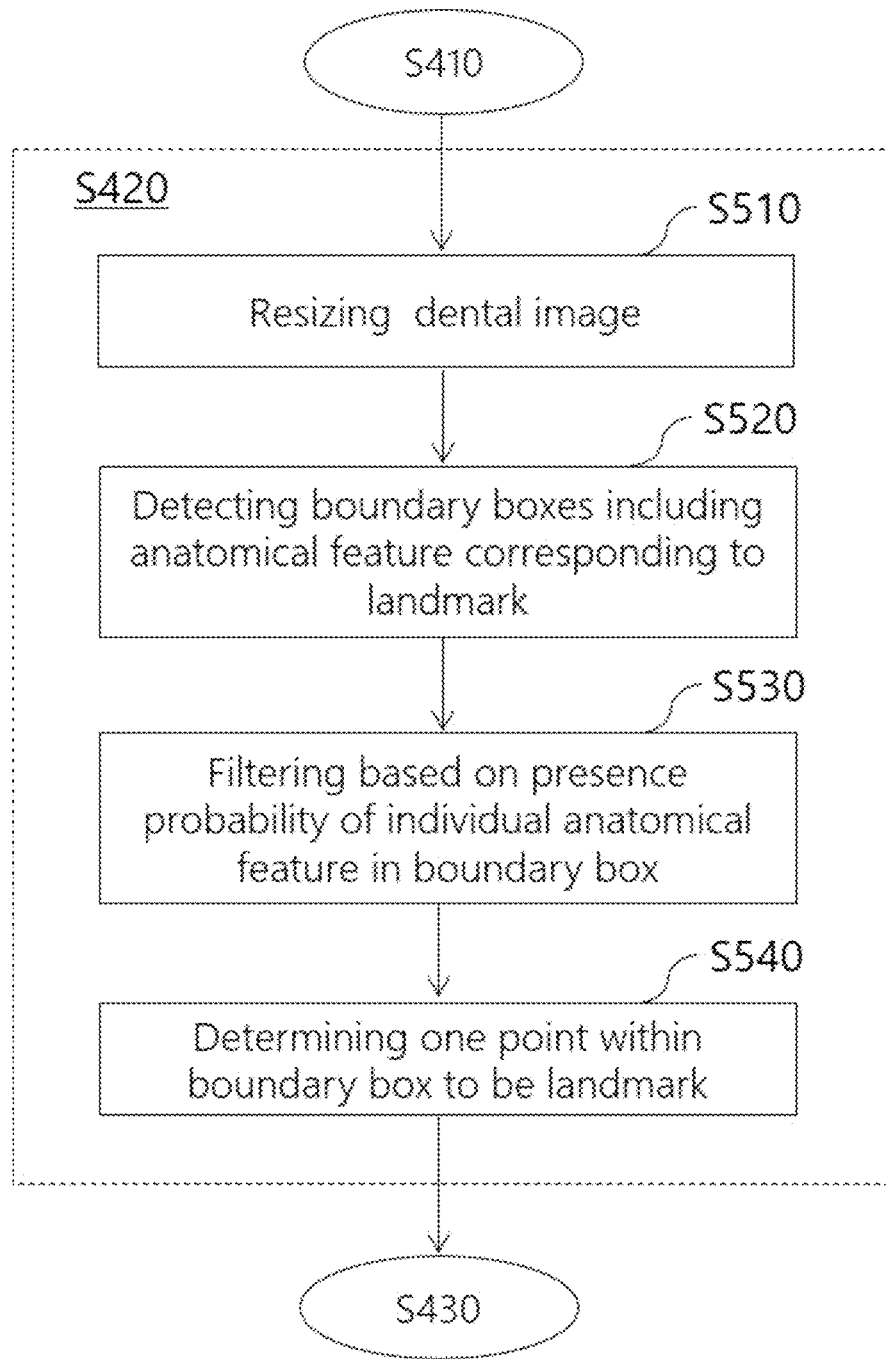
FIG. 5 shows an embodiment of step S420 in FIG. 4.

FIG. 4 shows a method of analyzing a dental image for correction diagnosis according to an embodiment of the present invention. FIG. 5 shows an embodiment of step S420 in FIG. 4.

In step S410, the image acquisition module 210 may obtain a dental image of an examinee from a different external computing device or another (a dental image photographing device, etc.) operating in conjunction with the computing device 100 through the communication unit 110. As described above, the dental image may be a cephalogram of the examinee.

In step S420, the landmark detection module 220 may detect at least some of a plurality of landmarks for correction diagnosis in the dental image of the examinee. In one embodiment, step S420 may include steps S510 to S540 as shown in FIG. 5.

In step S510, the landmark detection module 220 may resize the dental image. That is, the landmark detection module 220 may enlarge or reduce the dental image of the examinee at the same scale or ratio as a dental image previously learnt by the machine learning module 222. Accordingly, the method 400 according to the present invention can further improve detection accuracy of the machine learning module 222. The dental image may be implemented to be resized to 416×640 pixels, preferably.

In step S520, the machine learning module 222 may detect a plurality of boundary boxes predicted to include at least some of an individual anatomical feature corresponding to each of the plurality of landmarks in the dental image of the examinee based on the results of the learning of a plurality of accumulated comparison dental images, and may calculate the probability that each of the anatomical features will be present in each of the boundary boxes.

In one embodiment, step S520 may be performed through 3-step detection process depending on an abstraction degree of an image. That is, the dental image of the examinee is abstracted in different levels while experiencing a plurality of convolution layers included in the machine learning module 222. The machine learning module 222 may be implemented to detect a boundary box including an individual anatomical feature in the three different abstraction levels and to calculate the presence probability of the individual anatomical feature.

As the results of the execution of step S520, information about the center coordinates, size of a boundary box, and the presence probability of an individual anatomical feature may be generated as an output value with respect to each of the boundary boxes.

In step S530, the filtering module 224 may perform filtering on a boundary box based on the presence probability of an individual anatomical feature. For example, if two or more boundary boxes are detected with respect to one individual anatomical feature by applying the 3-step detection in step S520, the filtering module 224 may select one of the two or more boundary boxes as a boundary box in which the corresponding individual anatomical feature is present based on the presence probability. In one embodiment, the filtering module 224 may be implemented to select one boundary among the plurality of boundary boxes which has the highest presence probability of the corresponding individual anatomical feature.

In step S540, the landmark determination module 226 may determine one point within the filtered boundary box to be the coordinates of a landmark. For example, the landmark determination module 226 may determine the center coordinates of the detected boundary box to be the coordinates of a landmark corresponding to each individual anatomical feature.

Next, in step S430, the face shape determination module 240 may classify or determine a face shape of the examinee for correction treatment by performing cephalometric analysis based on at least some of the detected landmarks. For example, when some landmarks for calculating a meaningful straight line or angle necessary for cephalometric analysis are selected from the detected landmarks, the face shape determination module 240 classifies or determines a face shape of the examinee for correction treatment by automatically performing cephalometric analysis based on the selected landmarks. In this case, the face shape for correction treatment may include, for example, a hyperdivergent pattern, a normodivergent pattern, a hypodivergent pattern, and so on. According to embodiments applied to the present invention, the face shape may be classified in more various ways depending on the degree that the relative positions of the upper and lower jaws are protruded. When the face shape is determined as described above, a diagnostician can work out an overall plan regarding correction treatment based on the determined face shape.

Although not shown in FIGS. 4 and 5, in one embodiment, the method 400 may further include the step of training the machine learning module 222. For example, such training may be performed using a plurality of accumulated comparison dental images. That is, the machine learning module 222 may be implemented to be trained in such a manner that a medical specialist accumulates and collects dental images of examinees whose landmarks have been read and the dental images are input to the machine learning module 222 as training data. In this case, the size of the trained comparison dental image may be 416×640 pixels, for example.

Furthermore, in one embodiment, the method 400 may further include the step of displaying a detected landmark. That is, when the detection of landmarks is completed in step S420, the storage and transmission module 250 may transmit information about some of the detected landmarks to a display device or a different computing device coupled thereto through the communication unit 110, so the information is displayed to a diagnostician. In one embodiment, such display may be performed based on preferred landmark information of a diagnostician. In this case, the preferred landmark information may include information about at least one of the geographical area, alma mater of the diagnostician, a preferred academic tradition related to correction diagnosis, and the geographical area of an examinee. For example, the landmark detection module 220 or the storage and transmission module 250 may be implemented to select some landmarks based on preferred landmark information of a diagnostician and to transmit only information about the selected landmarks to a display device or to emphasize and display some landmarks selected from the display device using a given method.

Figure 6:
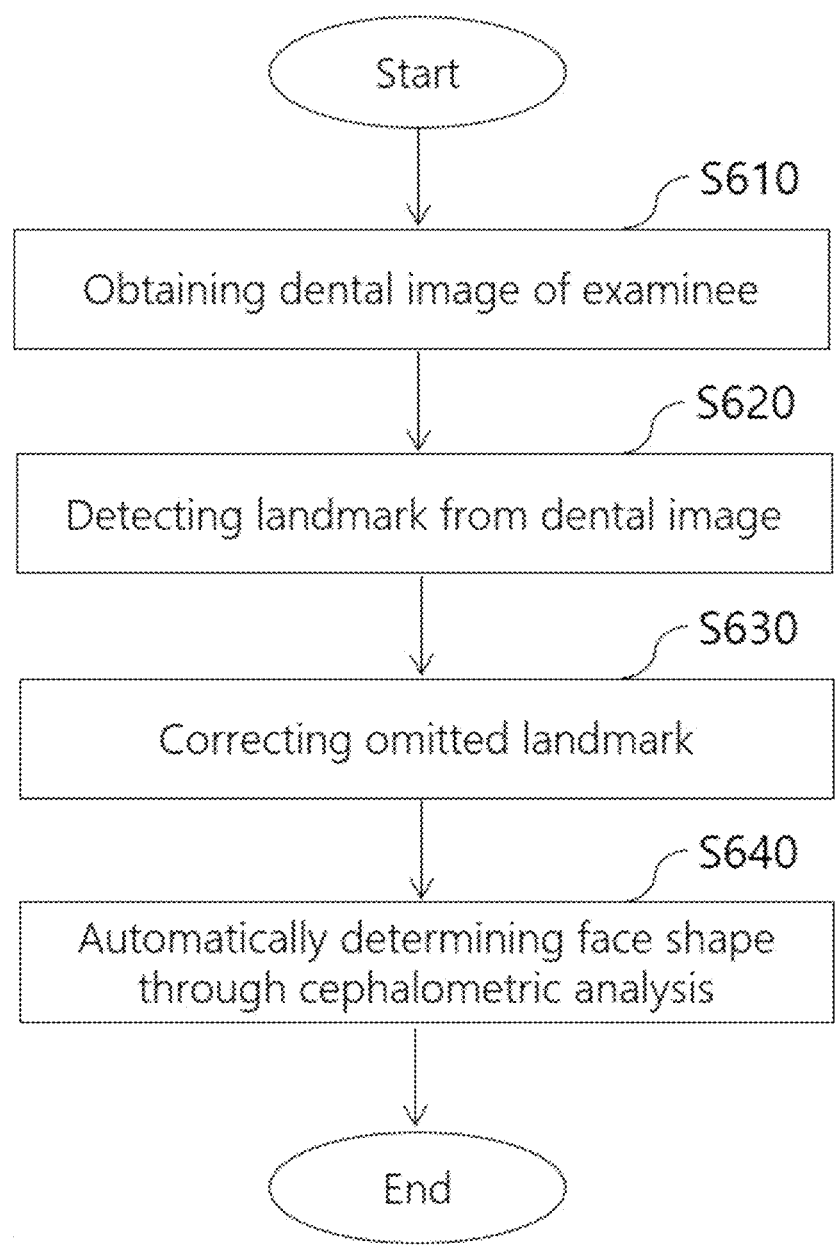
FIG. 6 shows a method of analyzing a dental image for correction diagnosis according to an embodiment of the present invention.
Figure 7:
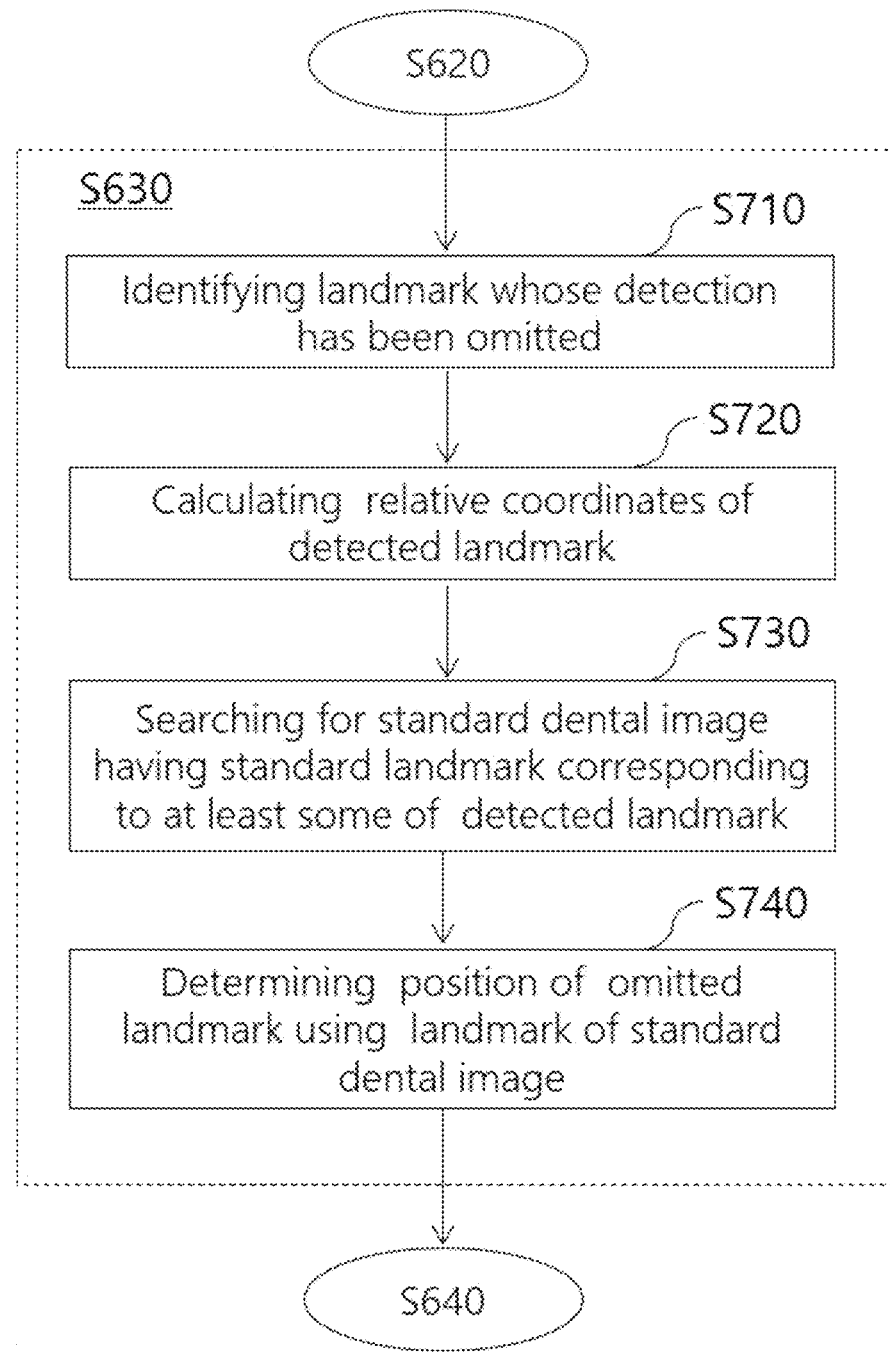
FIG. 7 shows an embodiment of step S630 in FIG. 6.

FIG. 6 shows a method of analyzing a dental image for correction diagnosis according to an embodiment of the present invention. FIG. 7 shows an embodiment of step S630 in FIG. 6.

In the method 600, steps S610, S620, and S640 are the same as steps S410 to S430 of the method 400 described with reference to FIGS. 4 and 5, and thus a detailed description thereof is omitted herein.

In step S630, if there is a landmark that belongs to the plurality of landmarks and that has not been detected in step S620, the landmark correction module 230 may correct the omitted landmark based on standard landmark information.

In this case, the standard landmark information may include information about a plurality of standard dental images, a plurality of the standard landmarks read with respect to each of the plurality of standard dental images and/or a plurality of adjacent landmarks disposed close to the standard landmarks. A standard dental image may be generated, for example, by extracting the presence area of a landmark whose landmark has been determined by a medical specialist. In this case, information about the standard landmarks may further include information about the relative coordinates of the standard landmarks in each standard dental image.

In one embodiment, step S630 may include steps S710 to S740 as shown in FIG. 7.

In step S710, the landmark correction module 230 may identify at least one landmark that has been omitted in step S620. That is, the landmark correction module 230 may identify an omitted landmark by comparing the detected landmarks with the plurality of landmarks set by a user or set by default.

In step S710, if the omitted landmark is not identified, steps S720 to S740 are not performed, and step S640 may be performed.

In step S720, the landmark correction module 230 may calculate the relative coordinates of at least some of the detected landmarks. For example, step S720 may be performed by extracting the area where a landmark is present from a dental image of an examinee whose landmark has been determined and normalizing the area in the same scale as a standard dental image. That is, as will be described with reference to FIGS. 10 and 11, after the area where a landmark is present is extracted from the dental image, the landmark correction module 230 may calculate at least one relative coordinates of the landmark as coordinates between (0, 0) to (1, 1) by converting the scale of the corresponding area.

In one embodiment, step S720 may be implemented to be performed on two or more landmarks positioned close to the omitted landmark.

In step S730, the landmark correction module 230 may search for a standard dental image having a standard landmark corresponding to at least some of the detected landmark using the calculated relative coordinates. For example, the landmark correction module 230 may search for a standard dental image having a standard landmark closest to an adjacent landmark of the omitted landmark by comparing the relative coordinates of a plurality of adjacent landmarks (preferably, 5 to 7 landmarks) disposed close to the omitted landmark with the relative coordinates of a plurality of adjacent landmarks disposed close to the standard landmark corresponding to the omitted landmark in each standard dental image.

In step S740, the landmark correction module 230 may determine the position (or coordinates) of the omitted landmark using the standard landmark of the retrieved standard dental image. That is, the landmark correction module 230 may set the relative coordinates of a standard landmark corresponding to the omitted landmark in the retrieved standard dental image as the relative coordinates of the omitted landmark, and may determine the position (or coordinates) of the omitted landmark by scaling the relative coordinates based on the original dental image.

Although not shown in FIGS. 6 and 7, in one embodiment, the method 600 may further include the step of training the machine learning module 222 again based on a finally corrected landmark and information about the dental image of the examinee. Detection accuracy of the machine learning module 222 can be further improved because the machine learning module 222 trains the corrected results of the omitted landmark again.

Figure 8:
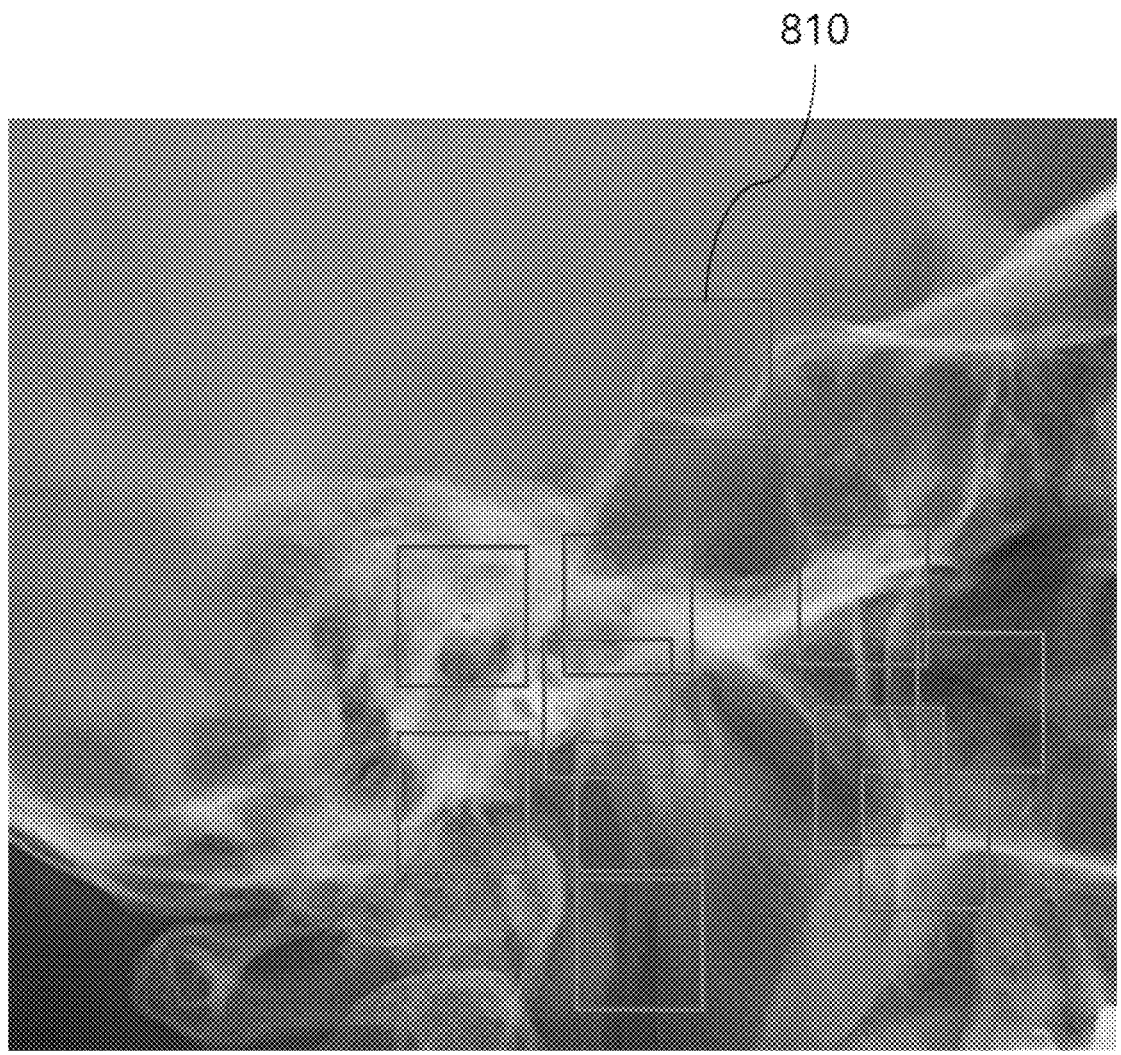
FIG. 8 illustrates boundary boxes for landmark detection in the method of analyzing a dental image for correction diagnosis according to an embodiment of the present invention.

FIG. 8 illustrates boundary boxes for landmark detection in the method of analyzing a dental image for correction diagnosis according to an embodiment of the present invention.

Referring to FIG. 8, a plurality of boundary boxes 810 may identify the areas where anatomical feature corresponding to a plurality of landmarks are defined from a dental image. In this case, the size of the area (label size) to define each individual anatomical feature may be set as 30×30 pixels, preferably, in order to maximize detection accuracy.

In one embodiment, the machine learning module 222 may split a dental image into a plurality of cells. A specific number of boundary boxes may be assigned with respect to each cell. If an individual anatomical feature is present in a specific cell, a boundary box assigned to the corresponding cell may be implemented to detect the individual anatomical feature.

Accordingly, as described above, the machine learning module 222 outputs information about the center coordinates (relative coordinates in each cell) and size (width, height) of each boundary box and the presence probability of each individual anatomical feature.

Figure 9:
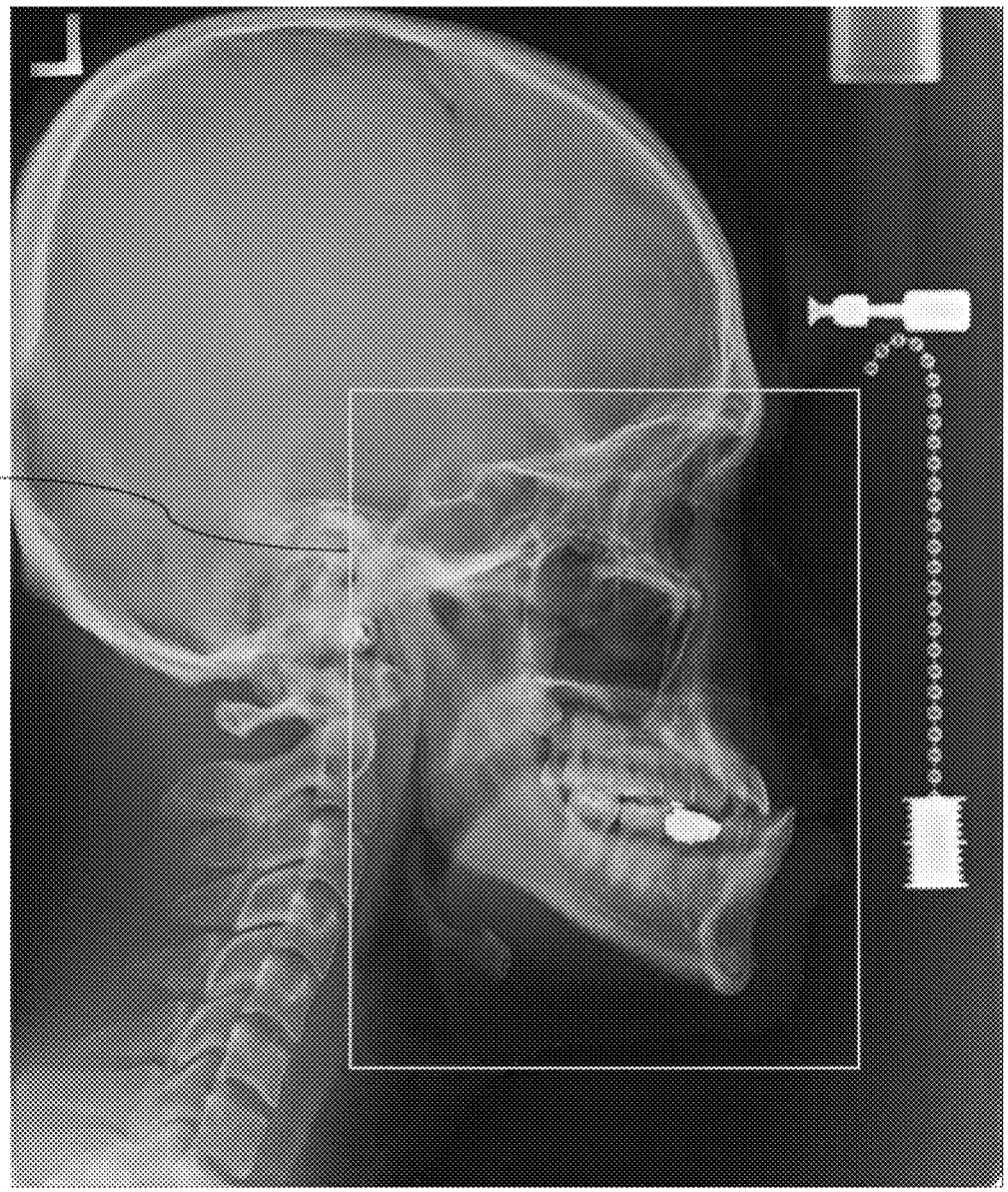
FIGS. 9 and 10 illustrate a process of generating a standard dental image in the method of analyzing a dental image for correction diagnosis according to an embodiment of the present invention.
Figure 10:
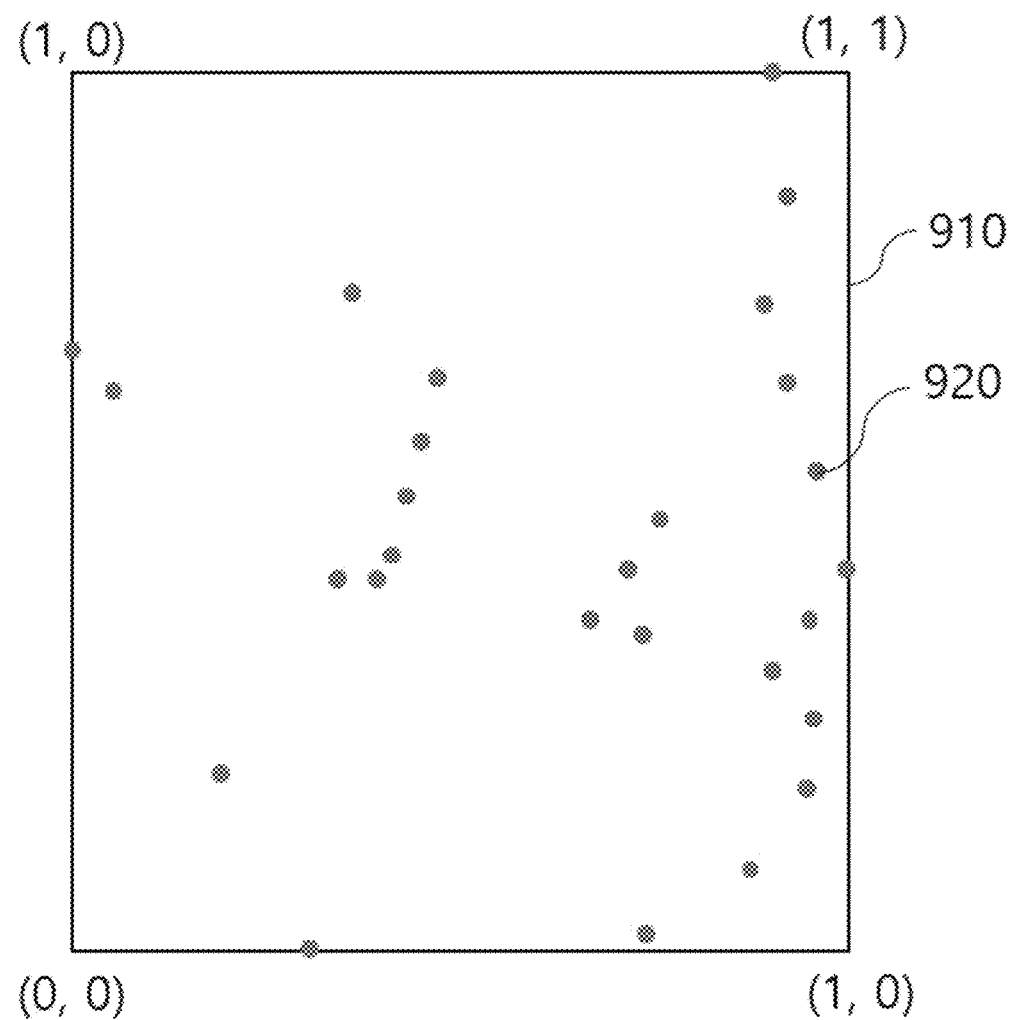

FIGS. 9 and 10 illustrate a process of generating a standard dental image in the method of analyzing a dental image for correction diagnosis according to an embodiment of the present invention.

Referring to FIGS. 9 and 10, the standard dental image may be generated based on a given original dental image whose landmark has been determined by a medical specialist. In this case, the original dental image may be at least some of a comparison dental image provided as the training data of the machine learning module 222.

That is, for example, the standard dental image may be generated by extracting the presence area of a standard landmark based on two or more outermost landmark in a standard dental image and then scaling the extracted area into a coordinate area corresponding to (0, 0) to (1, 1). Accordingly, each standard landmark within the converted coordinate area will have relative coordinates between (0, 0) to (1, 1).

Figure 11:
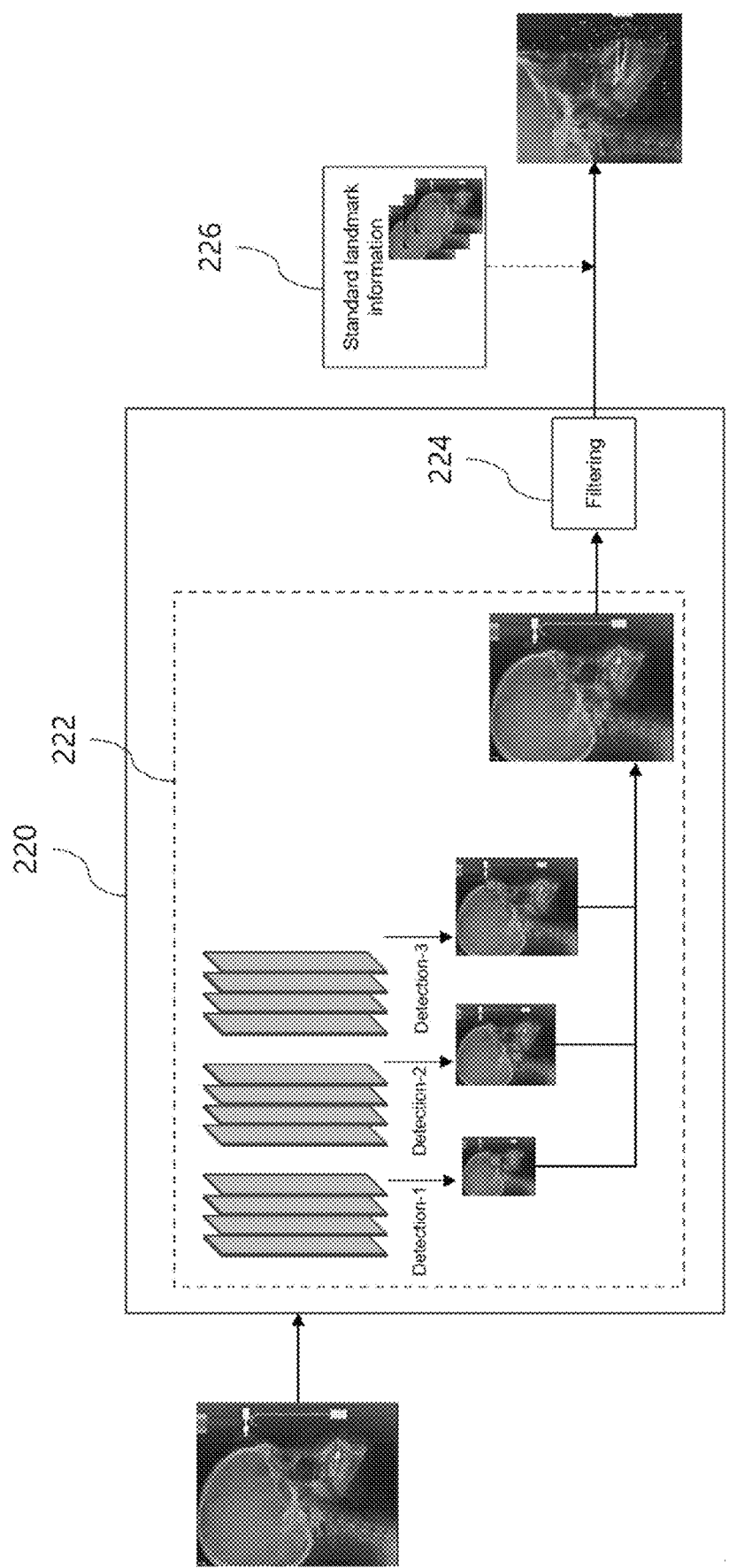
FIG. 11 illustrates a process of performing the method of analyzing a dental image for correction diagnosis according to an embodiment of the present invention.

FIG. 11 illustrates a process of performing the method of analyzing a dental image for correction diagnosis according to an embodiment of the present invention.

The process of executing the method of analyzing a dental image for correction diagnosis according to an embodiment of the present invention is listed as follows with reference to FIG. 11.

When a dental image of an examinee obtained through the image acquisition module 210 and the communication unit 110 is input to the machine learning module 222, the machine learning module 222 obtains a dental image through a plurality of convolution layers and detects a boundary box predicted to include an individual anatomical feature corresponding to each landmark in a 3-step level depending on an abstraction degree.

Next, if a plurality of boundary boxes for one individual anatomical feature is detected, the filtering module 224 filters a boundary box having the highest presence probability based on the presence probability of a corresponding anatomical feature. The landmark determination module 226 determines the center coordinates of a finally detected boundary box to be a landmark based on the results of the filtering.

Next, the landmark correction module 230 identifies whether a landmark whose detection has been omitted is present in a plurality of set landmarks, and determines the position (or coordinates) of the omitted landmark with reference to standard landmark information. All of finally set landmarks may be detected, and may be output to a display device, for example, in the form of coordinates or a point in such a way as to overlap a dental image.

Various embodiments described in this specification may be implemented by hardware, software and/or a combination of them. For example, the various embodiments may be implemented within one or more Application-Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, microcontrollers, microprocessors, other electronic units designed to the functions proposed herein or a combination of them.

Additionally, for example, the various embodiments may be written or encoded in a computer-readable medium including instructions. The instructions written or encoded in the computer-readable medium may enable a programmable processor or other processors to execute a method when instructions, for example, are executed. The computer-readable medium includes a computer storage medium. The storage medium may be a given available medium accessible by a computer. For example, the computer-readable medium may include RAM, ROM, EEPROM, CD-ROM or other optical disk storage media, magnetic disk storage media or other magnetic storage devices, or a given other medium which may be used to store desired program code in the form of instructions or data structures accessible by a computer.

Such hardware, software, etc. may be implemented within the same device or different devices to support the various operations and functions described in this specification. Additionally, elements, units, modules, components, etc. described as "~unit" in the present invention may be individually implemented as logic devices that may be driven together or mutually although they are individual. The description of different characteristics of the modules, the units, etc. has been intended to emphasize different functional embodiments, and it does not essentially mean that the different characteristics must be realized by individual hardware or software components. Rather, functions related to one or more modules or units may be performed by individual hardware or software components or may be integrated into common or individual hardware or software components.

Although the operations have been shown in the drawings in a specific sequence, it should not be understood that such operations must be performed in the illustrated specific sequence or sequentially in order to achieve desired results or all the illustrated operations must be performed. In a given environment, multi-tasking and parallel processing may be advantageous. Furthermore, it should not be understood that the division of various elements in the aforementioned embodiments is necessary in all the embodiments, but should be understood that the aforementioned elements may be integrated into a single software product or packaged into a multi-software product.

The best embodiments have been disclosed in the drawings and specification. Specific terms have been used herein, but the terms are used to only describe the present invention, but are not used to limit the meaning of the terms or the range of right of the present invention written in the claim. Accordingly, those skilled in the art will understand that various modifications and other equivalent embodiments are possible from the embodiments. Accordingly, the true technical range of protection of the present invention should be determined by the technical spirit of the following claims.

The invention claimed is:

1. A method of analyzing a dental image for a correction diagnosis, the method comprising:
   obtaining a dental image of an examinee and collectively abstracting the dental image; and
   detecting in the dental image a plurality of landmarks for the correction diagnosis using a landmark detection module,
   wherein each of the plurality of landmarks is an anatomical reference point indicative of a relative position of at least one of a facial skeleton, a tooth, and a face contour necessary for the correction diagnosis, and the landmark detection module comprises a machine learning module based on an artificial neural network,
   wherein in the detecting the plurality of landmarks, the landmark detection module simultaneously detects the plurality of landmarks based on a single convolution network,
   wherein the detecting the plurality of landmarks comprises:
      simultaneously detecting in the dental image a plurality of boundary boxes respectively predicted to include at least one anatomical feature corresponding to a respective landmark and detecting a center coordinate in each of the plurality of boundary boxes; and determining center coordinates of at least some of the plurality of boundary boxes to be one or more of the plurality of landmarks.

2. The method of claim 1, further comprising training the machine learning module using training data including a plurality of accumulated comparison dental images,
wherein each of the plurality of accumulated comparison dental images is a dental image of a different examinee whose respective plurality of landmarks have been identified by a medical specialist.

3. The method of claim 1, wherein the dental image is a cephalogram.

4. The method of claim 1, wherein the detecting the plurality of landmarks further comprises:
resizing the dental image,
wherein the detecting is performed based on the resized dental image.

5. The method of claim 1, wherein the detecting the plurality of landmarks further comprises:
calculating a presence probability of the at least one anatomical feature with respect to the each of the plurality of boundary boxes, and
wherein the determining the center coordinates comprises:
when multiple boundary boxes of the plurality of boundary boxes are predicted to include an identical anatomical feature, filtering one of the multiple boundary boxes based on the presence probability of the identical anatomical feature; and
determining a center coordinate included in the filtered one of the multiple boundary boxes to be one of the plurality of landmarks.

6. The method of claim 1, further comprising:
receiving preferred landmark information of a diagnostician; and
emphasizing and displaying some of the detected plurality of landmarks corresponding to the preferred landmark information.

7. The method of claim 1, further comprising determining, for a correction treatment, a face shape of the examinee by performing cephalometric analysis based on the detected plurality of landmarks.

8. A non-transitory computer-readable recording medium in which a program for executing a method according to claim 1 is written.

9. A method of analyzing a dental image for a correction diagnosis, the method comprising:
obtaining a dental image of an examinee; and
detecting in the dental image a plurality of landmarks for the correction diagnosis using a landmark detection module,
wherein each of the plurality of landmarks is an anatomical reference point indicative of a relative position of at least one of a facial skeleton, a tooth, and a face contour necessary for the correction diagnosis, and the landmark detection module comprises a machine learning module based on an artificial neural network,
the method further comprising:
identifying an omitted landmark by comparing the detected plurality of landmarks with a plurality of preset landmarks;
searching, based on standard landmark information, for a standard dental image having at least one standard landmark corresponding to at least one of the detected plurality of landmarks, wherein the standard landmark information comprises information about a plurality of standard dental images and each of a plurality of standard landmarks identified with respect to each of the plurality of standard dental images; and
determining a position of the omitted landmark using the standard dental image and the at least one standard landmark of the standard dental image.

10. The method of claim 9, wherein the standard landmark information further comprises information about a plurality of adjacent landmarks disposed near each of the at least one standard landmark, and
wherein in the searching for the standard dental image, the standard dental image having a set of standard landmarks corresponding to a set of adjacent landmarks adjacent to the omitted landmark among the detected plurality of landmarks is searched for based on the information about the plurality of adjacent landmarks.

11. The method of claim 9, wherein the standard dental image is generated by extracting a presence area of the at least one standard landmark from an original dental image,
wherein the standard landmark information further comprises information about relative coordinates of the at least one standard landmark in the standard dental image,
wherein the method further comprises calculating respective relative coordinates of the detected plurality of landmarks by extracting a presence area of each of the detected plurality of landmarks from the dental image and normalizing the extracted presence area at an identical scale as the standard dental image, and
wherein the searching for the standard dental image and the determining the position of the omitted landmark are performed based on the calculated respective relative coordinates of the detected plurality of landmarks and the relative coordinates of the at least one standard landmark.

12. A computing device supporting analysis of a dental image for a correction diagnosis, the computing device comprising at least one processor configured for:
obtaining the dental image of an examinee and collectively abstracting the dental image; and
detecting from the dental image at least a plurality of landmarks for the correction diagnosis,
wherein each of the plurality of landmarks is an anatomical reference point indicative of a relative position of at least one of a facial skeleton, a tooth, and a face contour necessary for the correction diagnosis, and the at least one processor includes the landmark detection module which comprises a machine learning module based on an artificial neural network,
wherein the landmark detection module is configured to simultaneously detect the plurality of landmarks based on a single convolution network at least by:
simultaneously detecting in the dental image a plurality of boundary boxes respectively predicted to include at least one anatomical feature corresponding to a respective landmark and detecting a center coordinate in each of the plurality of boundary boxes; and
determining center coordinates of at least some of the plurality of boundary boxes to be one or more of the plurality of landmarks.

* * * * *